(12) United States Patent
Annis et al.

(10) Patent No.: US 8,096,970 B2
(45) Date of Patent: *Jan. 17, 2012

(54) DIAPHRAGM PUMP WITH PROPHYLACTIC COVER

(75) Inventors: Larry D. Annis, Elgin, IL (US); Brian H. Silver, Cary, IL (US); Michael Dettling, Lauerz (CH)

(73) Assignee: Medela Holding AG, Baar (CH)

( * ) Notice: Subject to any disclaimer, the term of this patent is extended or adjusted under 35 U.S.C. 154(b) by 1164 days.

This patent is subject to a terminal disclaimer.

(21) Appl. No.: 11/891,536

(22) Filed: Aug. 10, 2007

(65) Prior Publication Data

US 2008/0033352 A1     Feb. 7, 2008

Related U.S. Application Data (60) Continuation-in-part of application No. 10/413,463, filed on Apr. 14, 2003, which is a continuation-in-part of application No. 10/114,686, filed on Apr. 2, 2002, now Pat. No. 6,808,517, which is a continuation-in-part of application No. 09/476,076, filed on Dec. 30, 1999, now abandoned, said application No. 11/891,536 is a continuation-in-part of application No. 09/475,681, filed on Dec. 30, 1999, now Pat. No. 6,547,756, and a continuation-in-part of application No. 09/591,749, filed on Jun. 12, 2000, now Pat. No. 7,255,681, which is a division of application No. 09/055,101, filed on Apr. 3, 1998, now Pat. No. 6,257,847, which is a continuation-in-part of application No. 08/510,714, filed on Aug. 3, 1995, now Pat. No. 5,776,098.

(60) Provisional application No. 60/170,070, filed on Dec. 10, 1999.

(51) Int. Cl.
*A61M 1/06* (2006.01)

(52) U.S. Cl. .......................................................... 604/74

(58) Field of Classification Search ............... 604/74–76
See application file for complete search history.

(56) References Cited

U.S. PATENT DOCUMENTS

| | | | | |
|---|---|---|---|---|
| 4,799,922 A * | 1/1989 | Beer et al. | ...... | 604/74 |
| 4,813,932 A * | 3/1989 | Hobbs | ...... | 604/74 |
| 5,009,638 A * | 4/1991 | Riedweg et al. | ...... | 604/74 |
| 5,071,403 A * | 12/1991 | Larsson | ...... | 604/74 |
| 5,358,476 A * | 10/1994 | Wilson | ...... | 604/74 |
| 5,571,084 A * | 11/1996 | Palmer | ...... | 604/74 |
| 5,776,098 A * | 7/1998 | Silver et al. | ...... | 604/74 |
| 6,110,140 A * | 8/2000 | Silver | ...... | 604/74 |
| 6,699,213 B1 * | 3/2004 | Annis et al. | ...... | 604/74 |
| 6,749,582 B2 * | 6/2004 | Britto et al. | ...... | 604/74 |

* cited by examiner

*Primary Examiner* — Jackie Ho
*Assistant Examiner* — Andrew Gilbert
(74) *Attorney, Agent, or Firm* — McDonnell Boehnen Hulbert & Berghoff LLP (57) ABSTRACT

A device for protecting the diaphragm of a pump, such as a diaphragm pump for a breastpump, from fluid (air/milk) is disclosed. A mounted flexible cover is located between the shell of the pump and the movable diaphragm membrane within the shell which isolates the membrane from fluid.

12 Claims, 9 Drawing Sheets

DIAPHRAGM PUMP WITH PROPHYLACTIC COVER

RELATED PATENT APPLICATIONS

This application is a continuation-in-part of Ser. No. 10/413,463, filed Apr. 14, 2003, which is a continuation-in-part of both U.S. patent application Ser. No. 09/475,681, filed Dec. 30, 1999 (now U.S. Pat. No. 6,547,756), and U.S. patent application Ser. No. 10/114,686, filed Apr. 2, 2002 (now U.S. Pat. No. 6,808,517), which is a continuation-in-part of U.S. patent application Ser. No. 09/476,076, filed Dec. 30, 1999 (now abandoned), all of which claim the benefit of U.S. Provisional Application No. 60/170,070, filed Dec. 10, 1999.

This application is also a continuation-in-part of U.S. patent application Ser. No. 09/591,749 filed Jun. 12, 2000 (now U.S. Pat. No. 7,255,681), which is a divisional of U.S. patent application Ser. No. 09/055,101 filed Apr. 3, 1998 (now U.S. Pat. No. 6,257,847), which is a continuation-in-part of U.S. patent application Ser. No. 08/510,714 filed Aug. 3, 1995 (now U.S. Pat. No. 5,776,098).

FIELD OF THE INVENTION

This invention relates to breastpumps for drawing breastmilk, and particularly to a motorized, such as electrically driven, breastpump.

BACKGROUND

Breastpumps for use by nursing mothers are well known. They allow the nursing woman to express the breastmilk as necessary or convenient, and further provide collection of the breastmilk for later use. For some mothers, breastpumps may be a necessity, such as when the child has suckling problems, or if the mother has problems with excessive or deficient milk production, or soreness, deformation or injury of the mammilla.

Manual breastpumps are commonplace, primarily because they are relatively inexpensive and easy to transport. Being manually driven, however, stroke rate and suction pressure produced can be uneven, and operating the pump can ultimately be tiring.

Electrically-driven breastpumps are also commonplace. They may be of a substantially large size of a non-portable or semi-portable type, typically including a vacuum pump which has an electric motor that plugs into standard house current. Advantages of this type of pump are ready controllability and regulation of the vacuum, and the ability to pump both breasts at once. That is, the nursing woman has both hands free to hold two breastpump shields in place for pumping of both breasts at the same time.

Battery-driven breastpumps have also been developed. These breastpumps have the advantages of controllability and regulation of the vacuum, as well as being easily carried. Such a battery-driven portable breastpump is described in U.S. Pat. No. 4,964,851, for example. This breastpump, sold under the name MINIELECTRIC by Medela, Inc., is lightweight and achieves good vacuum (i.e., negative pressure) regulation in preferred limits, for example, between about 100 and about 220 mmHg. The LACTINA breastpump sold by Medela, Inc. is also another type of breast pump which may be driven by battery as well as house current. It is generally disclosed in U.S. Pat. No. 5,007,899.

Breastpumps, such as the foregoing motorized pumps, typically have internal workings that should be isolated from milk and other fluids and material. This is particularly true where such pumps may be used by many women, such as in hospital or rental settings.

SUMMARY

One aspect of the present invention is a breastpump assembly having a prophylactic device for protecting the diaphragm from fluid (air/milk). In one embodiment of this aspect of the invention, a diaphragm pump for a breastpump comprises a shell having a generally hemispherical interior shape with a flexible membrane movable within the hemispherical shape to expand and contract a volume created in a chamber defined between the membrane and the shell. A mechanism connected to the membrane, such as a puller, moves the membrane to expand and contract the volume. A port is provided in the shell through which air moves in response to expansion and contraction of the volume, such that vacuum can be communicated to a breastshield through connection to the port.

A mounted flexible cover is located between the shell and the membrane which isolates the membrane from fluid. The membrane has a circumferential rim upon which the cover is received over the rim. The shell has an internal opening defined therein sized to encompass the rim with the cover mounted on the rim in a substantially airtight fit. The flexible cover thereby forms a gasket between the rim and shell. A one-way valve extending through the membrane is additionally provided, allowing exhaustion of air between the membrane and cover.

The protective cover may be made removable and/or disposable. The protective cover may also be made as a more or less permanent element of the breastpump assembly, in that it is not expressly removable or disposable, but is still cleanable in situ nevertheless.

These as well as other aspects and advantages will become apparent to those of ordinary skill in the art by reading the following detailed description, with reference where appropriate to the accompanying drawings. Further, it is understood that this summary is merely an example and is not intended to limit the scope of the invention as claimed.

BRIEF DESCRIPTION OF THE DRAWINGS

Certain examples are described below in conjunction with the included figures, wherein like reference numerals refer to like elements in the various figures, and wherein.

DETAILED DESCRIPTION

Figure 1:
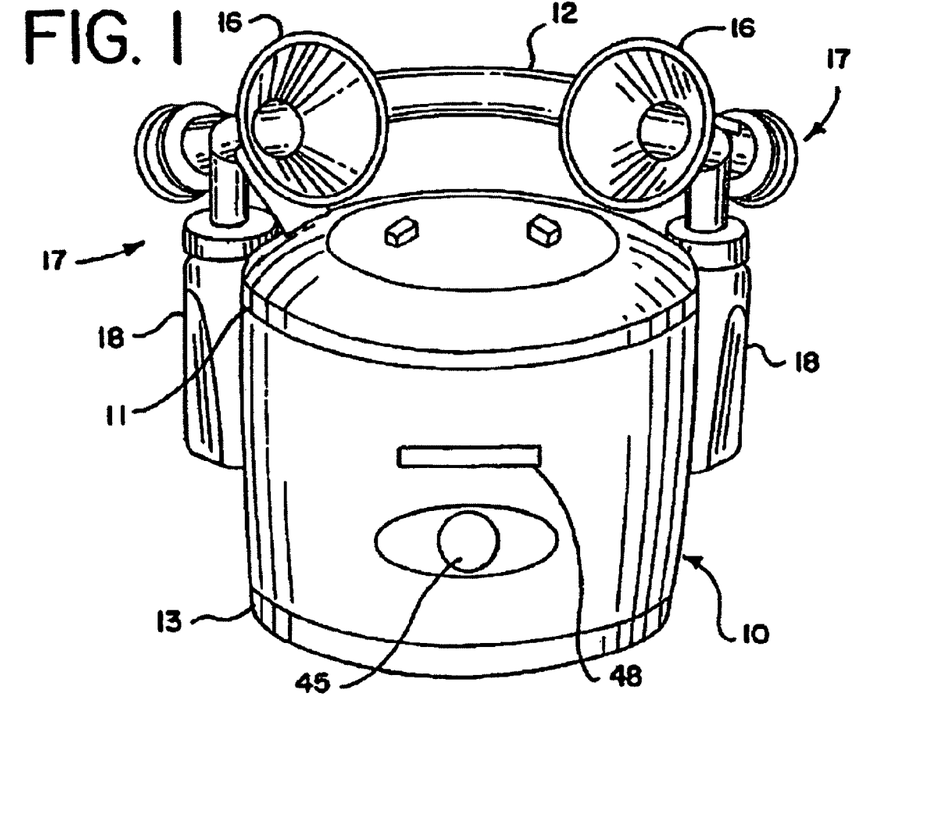
FIG. 1 is a front perspective view of a breastpump assembly made in accordance with aspects of the present invention.
Figure 2:
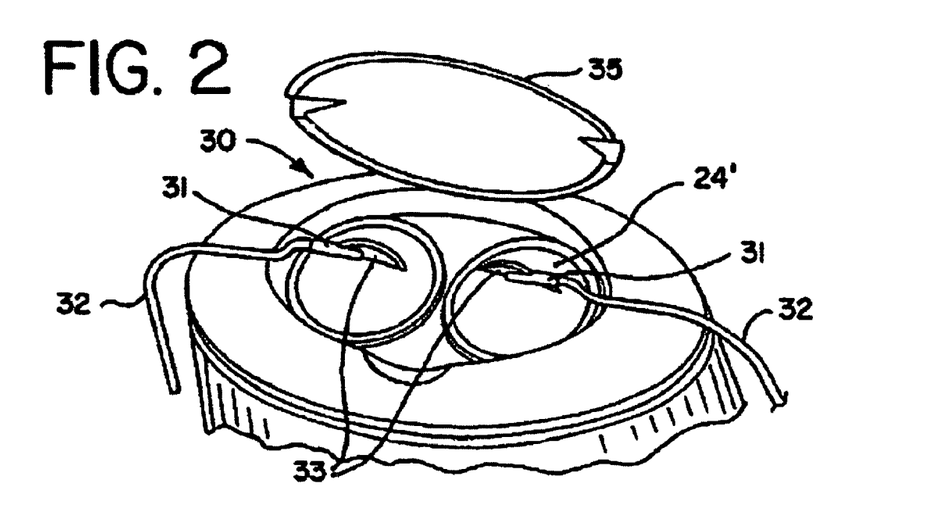
FIG. 2 is a top view of the breastpump of FIG. 1 with a cover removed revealing diaphragm pumps.
Figure 3:
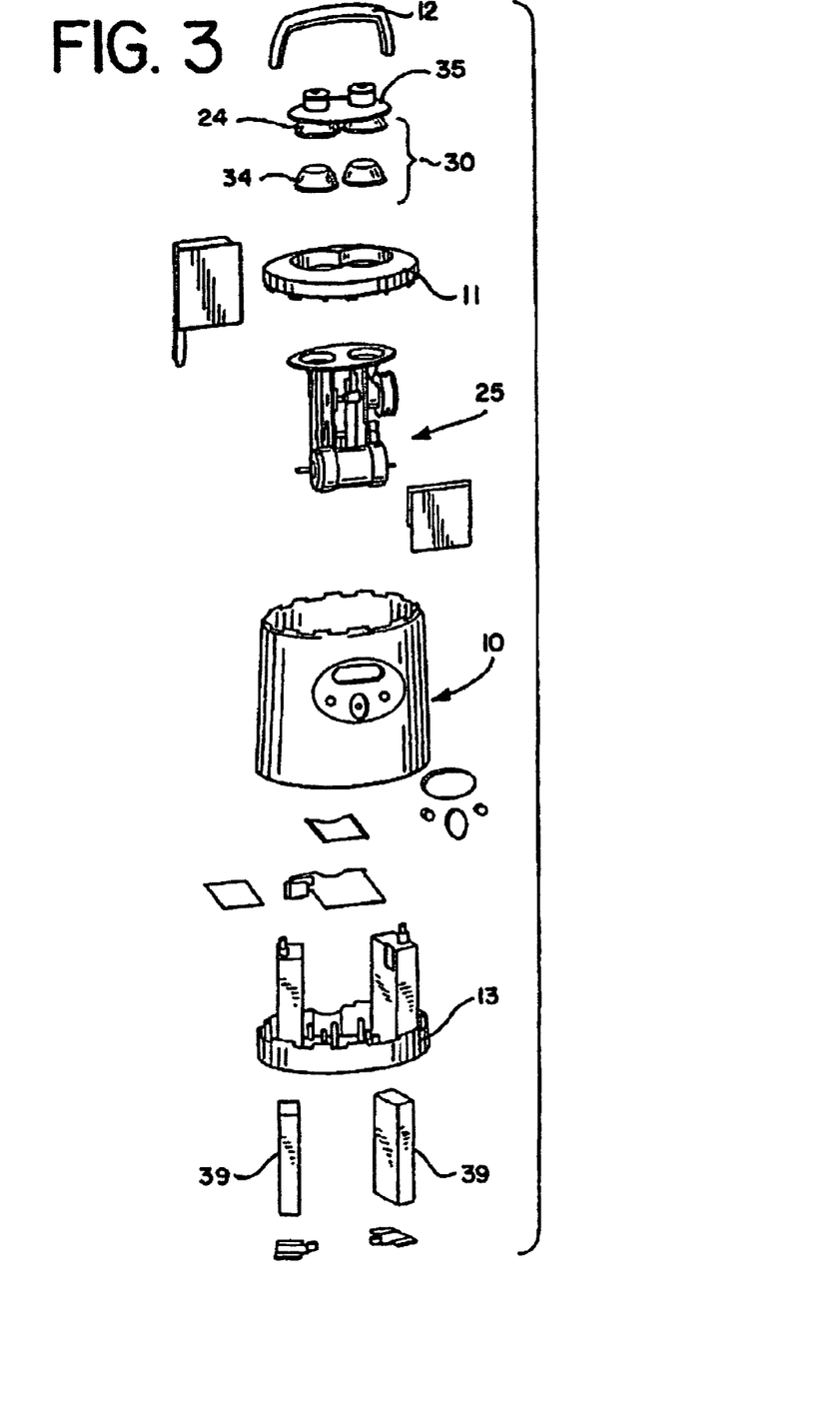
FIG. 3 is a somewhat exploded assembly view of the major components of the breastpump of FIGS. 1 through 2, with a modified top cover for the diaphragm pump assembly.

Referring to FIGS. 1 through 3 initially, a breastpump assembly of the present invention in one form has a casing 10 with a drive unit 25 mounted therein. There are, of course, any number of drives that may be used for diaphragm pumps such as those used in the instant embodiment. Indeed, the type of drive unit is not necessarily significant to certain aspects of the present invention. The drive unit 25 generates a linear movement (push and pull) that drives a pair of diaphragm pumps 30.

The drive unit 25 engages the diaphragm pumps 30 through mechanical coupling with the interior of a respective diaphragm membrane member 34. The linear pulling motion of the drive unit causes a negative pressure, or vacuum, to be generated in the pair of diaphragm pumps 30. Each diaphragm pump has a flexible membrane 34 mounted in the upper housing 11 assembled with a respective rigid shell 24 (and see FIGS. 6 and 7(a) through 7(c) described further below). The membrane 34 and shell 24 are in substantially airtight engagement. When the membrane 34 is pulled away from the shell 24, a vacuum is generated in the space between the shell interior and the membrane, which can be accessed through outlet port 31 formed on the shell, to which a tube 32 is connected to communicate the vacuum to a respective breastshield 17.

Figure 4:
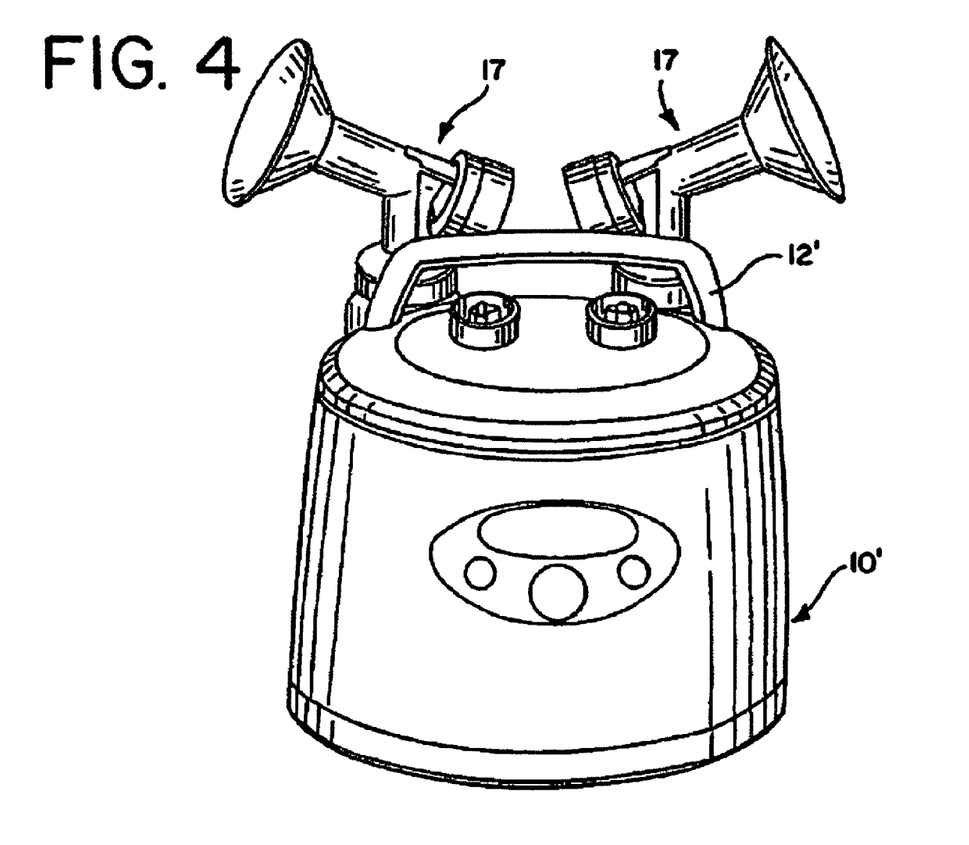
FIG. 4 is a front perspective view of another embodiment of a breastpump assembly made in accordance with aspects of the invention.

It will be noted that the FIG. 4 embodiment is substantially the same as that of FIGS. 1 through 3, except for a modified cover for the upper housing. In the embodiment of FIG. 4, the rigid shells 24 for the diaphragms are formed as part of the cover 35. In all other respects, the functionality of the diaphragm pump of FIG. 1 through 3 is substantially similar to the embodiment of FIG. 4, as further described below.

FIG. 4 shows another version of a breastpump of the present invention substantially the same as that of FIGS. 1 through 3, except with a modified cover 35'' and shell 24' (primed numbers being substantially similar to their un-primed counterparts) for the diaphragm pump 30. In one embodiment, the two diaphragm pumps 30 are in a well formed in the top of the casing 10. A cover 35 (also 35' and 35'') is provided which fits over the well and is generally flush with the upper housing part 11. The outlets 31 extend through relieved areas in the cover 35, for example, for easy access in use.

As noted above, in the embodiment of FIG. 3 the shells 24 are shown formed in the cover 35. The embodiment of FIG. 5 has the shells 24 mounted in the upper housing, as through a snap fit or interference engagement, such as shown in the embodiment of FIGS. 6 and 7(a) through 7(c), to allow easier access for cleaning or replacing the membranes of the pumping mechanism, and for cleaning the shells themselves (which are provided with grips 33 to these ends).

Figure 5:
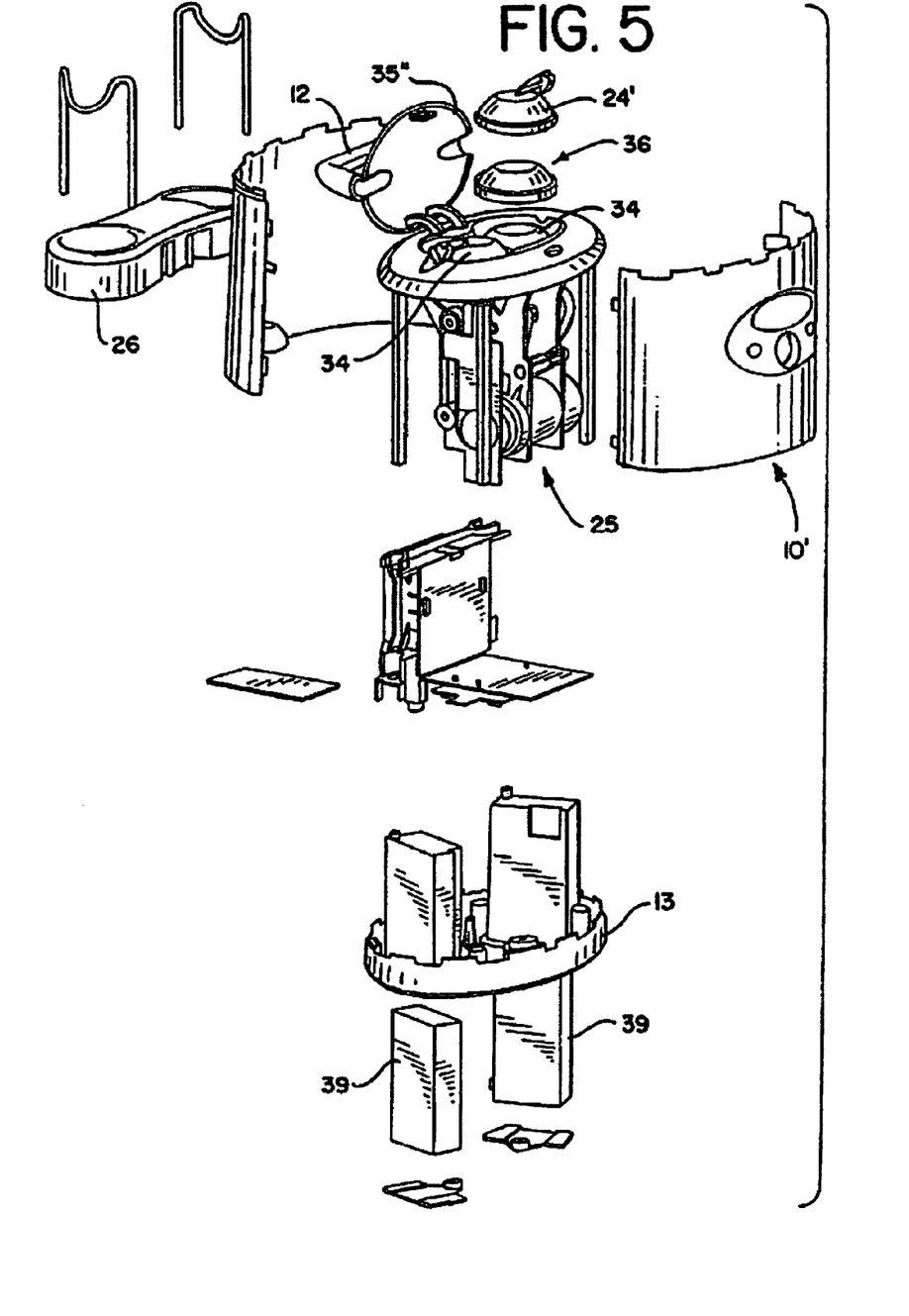
FIG. 5 is a somewhat exploded assembly view of the major components of yet another breastpump made in accordance with the present invention.
Figure 6:
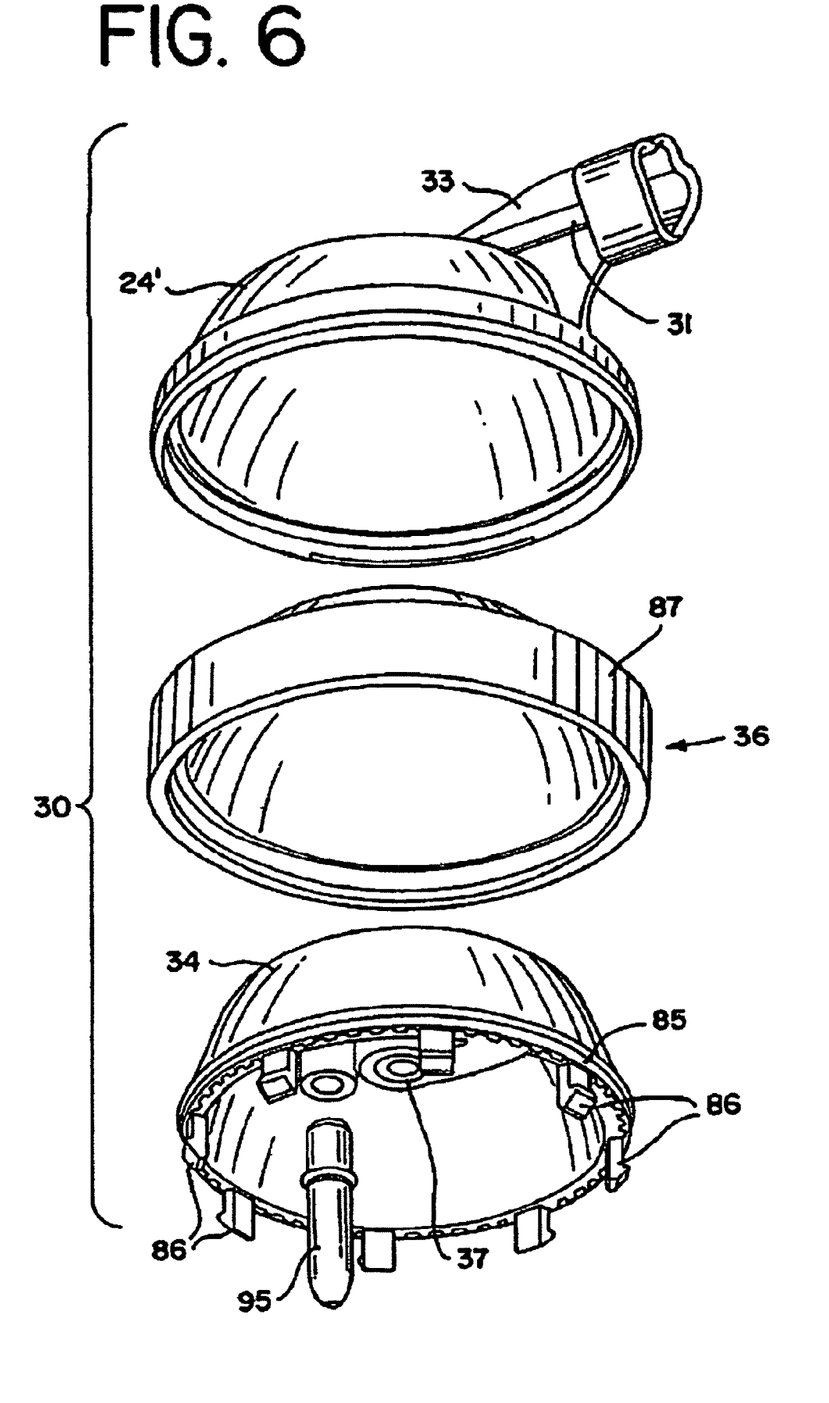
FIG. 6 is an enlarged assembly view of the diaphragm pump mechanism.
Figure 7A:
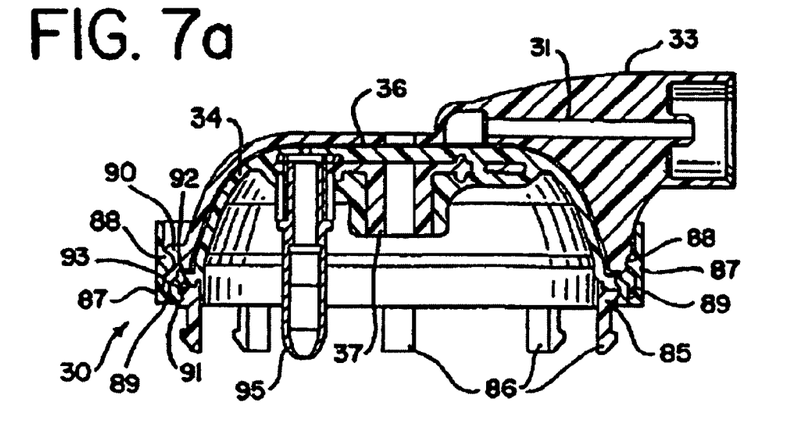
FIG. 7(a) is a cross-sectional view of the assembled diaphragm pump of FIG. 5.
Figure 7B:
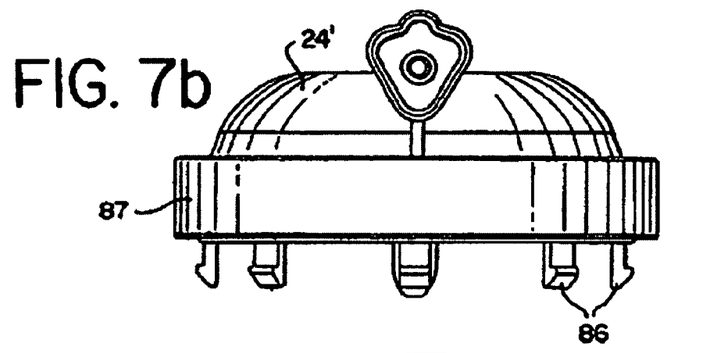
FIG. 7(b) is an elevational view of the assembled diaphragm pump of FIG. 5.
Figure 7C:
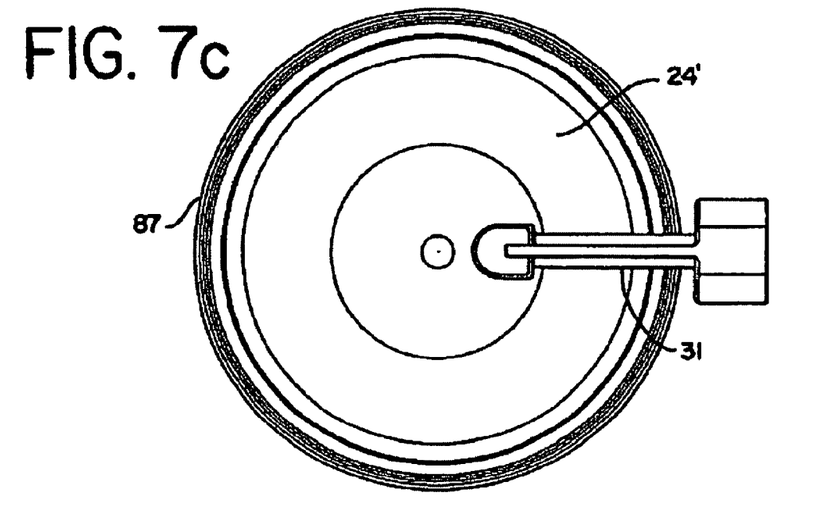
FIG. 7(c) is a top view of the assembled diaphragm pump of FIG. 5.
Figure 8:
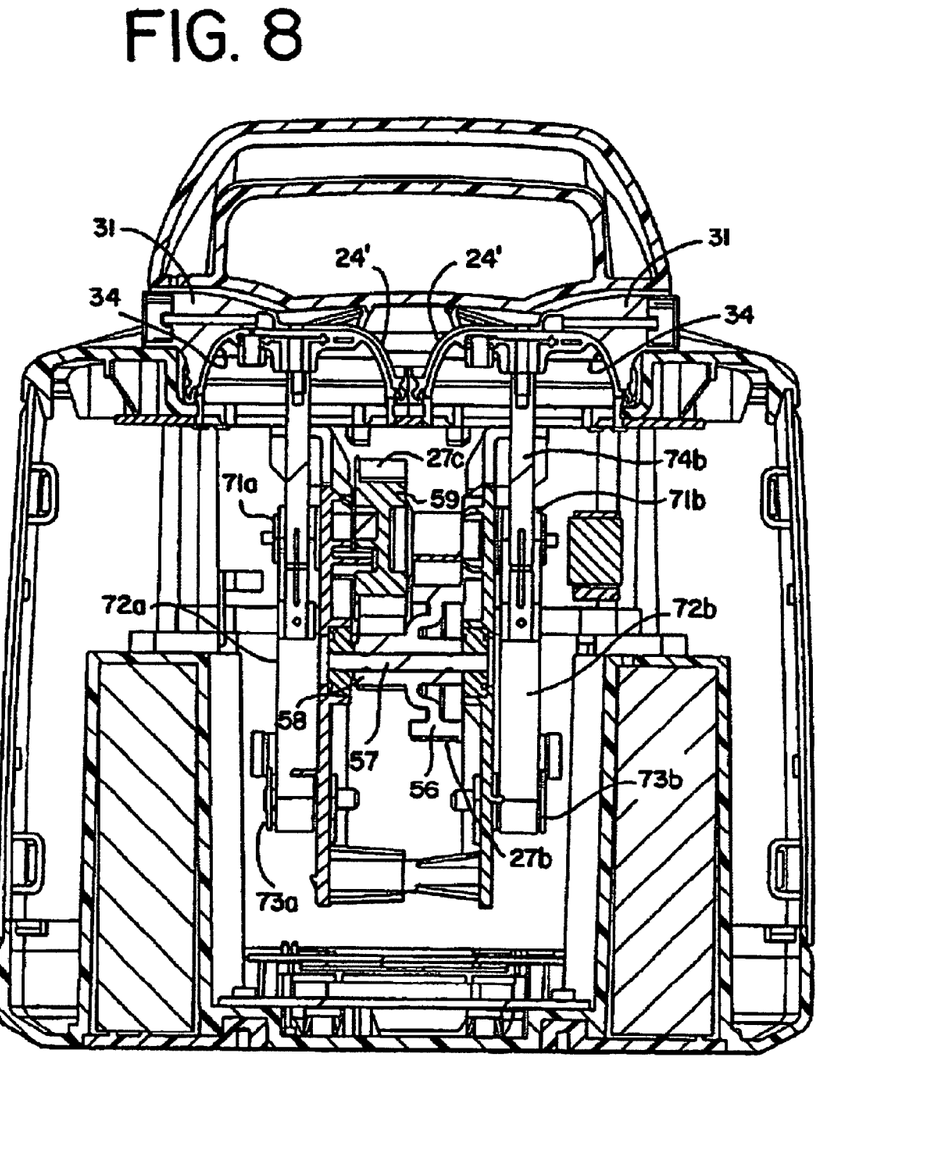
FIG. 8 is a sectional view of the assembled breastpump of FIG. 4 taken through the middle of the breastpump along its long lateral axis (side to side) looking rearwardly.

In the embodiment of FIG. 5, diaphragm member or membrane 34, which may be made of any suitably durable flexible and durable fluid-impervious material (to be airtight), such as silicone with a Shore A hardness in the range of 30 to 70, is molded around its perimeter to a rigid plastic collar 85. Collar 85 has a plurality of depending anchor posts 86 with outboard flanges formed thereon, which engage with the inside lip of the respective well in the upper housing part 11 within which the collar 85 is received to snap-fit the membrane 34 in place.

In addition, prophylactic (protective) covers 36 may be advantageously provided, which form-fit over the diaphragms 34 and isolate them from air and other fluid from the breastshields. The covers 36, which can be made of the same material as the membranes, are likewise fluid-impervious.

Referring to FIGS. 6 and 7(a) through 7(c) in particular, each of the covers 36 has an upturned cuff 87 which forms an annular well around the perimeter of the cover 36. A pair of circumferential beads 88 and 89, which are slightly offset vertically from each other, are formed along the bottom area of the annular well. Uppermost bead 88 engages in an annular rim channel 90 formed along the bottom outside of shell 24', for a substantially airtight engagement between the protective cover 36 and the shell.

An interior channel 93 is formed within the interior bottom of the cover 36 by a bead 91 and shoulder 92, which each run circumferentially around the cover. This interior channel 93 is received on a slightly protruding edge or rim on the collar 85 of the membrane 34. An airtight fit is thus provided between the protective cover 36 and the membrane 34, which also serves to fix the shell 24 in place over the membrane 34, and complete the diaphragm pump 30.

Note also that a one-way valve 95 is provided in the membrane 34, which communicates with the possible space that may form between the membrane 34 and overlying cover 36. This valve permits any entrapped air between the membrane 34 and the overlying cover 36 to be exhausted, such as if the first stroke on start-up happens to be toward the shell 24, with the protective cover 36 thereafter then following the movement of the diaphragm 34 to which it will generally be in facial engagement.

Figure 9:
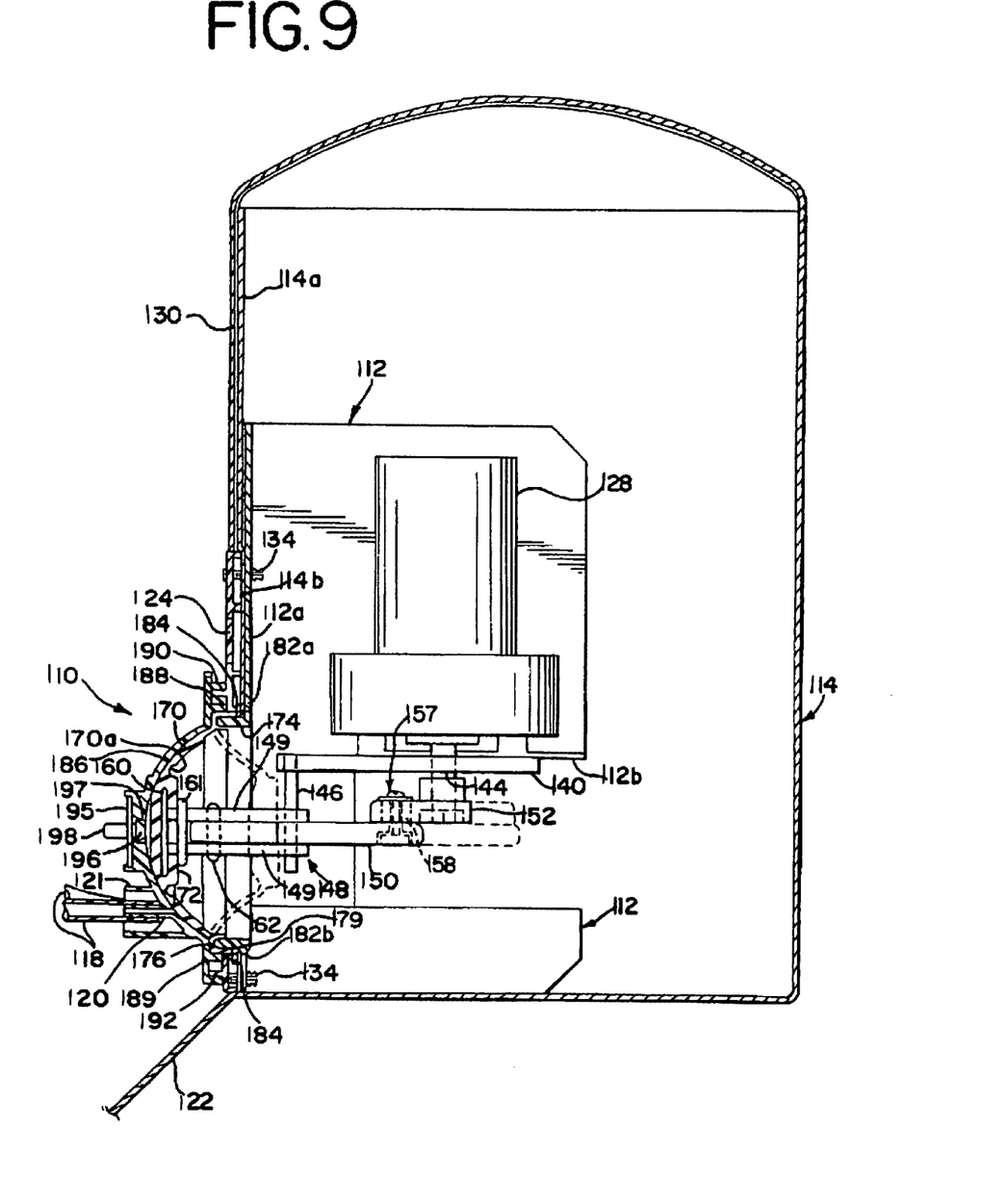
FIG. 9 is a cross-sectional view of yet another embodiment of a breastpump assembly made in accordance with aspects of the invention.
Figure 10:
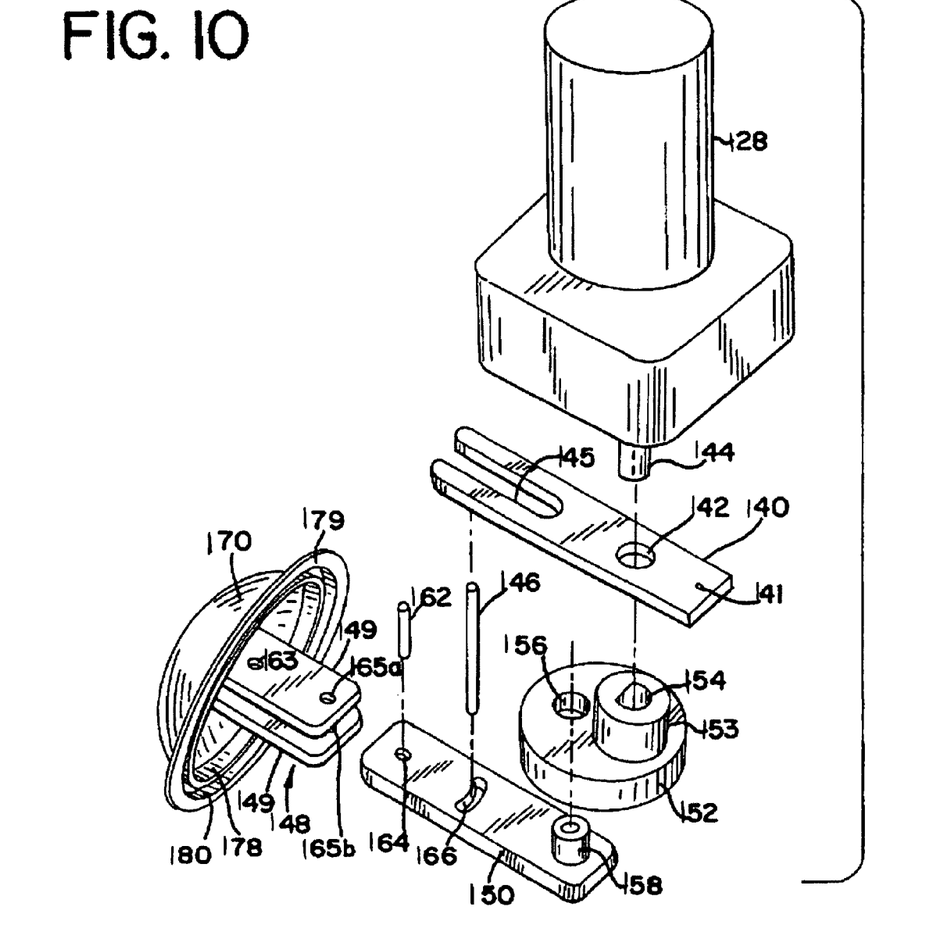
FIG. 10 is an exploded perspective view of several elements of the diaphragm pump of the assembly of FIG. 9.

Referring to FIGS. 9 and 10, yet another embodiment of a diaphragm pump assembly is illustrated. In this embodiment, diaphragm 170 is mounted to the front plate 124 of the assembly using a diaphragm mounting ring 174. Diaphragm 170 has a perimetrical shoulder 176 formed thereon from which depend inner and outer concentric circular flanges 178 and 180, respectively. Overlying the diaphragm 170 is a rigid housing cap 186 made of polypropylene. Cap 186 has an inner surface roughly matching the curvature of the diaphragm 170, such that the diaphragm rests close to or against the interior surface of the cap 186.

A thin disposable membrane-like cover (not shown) may additionally be provided over the diaphragm 170. This disposable cover would be between the diaphragm 170 and inside of the cap 186, and serve to further hygienically isolate the diaphragm 170 from any milk, air or the like which could be pulled within the cap 186 in the vacuum stroke. This disposable cover would be particularly useful if there were multiple users of the pump. The protective cover may, of course, be made non-removable. It would then be cleanable in situ, while still providing the desired isolation of the membrane and other inner workings of the pumping mechanism.

Further details of the foregoing embodiments may be gleaned from U.S. Pat. Nos. 5,776,098 and 6,547,756, the disclosures of which are hereby incorporated in herein in their entirety, as if specifically set forth in this application. In that regard, it should be noted that the numbered elements in FIGS. 9 and 10 that are not specifically addressed in this text are the same elements described in the foregoing U.S. Pat. No. 5,776,098 with a leading "1" added thereto (e.g., element 112 herein is element 12 therein).

While the invention has been described herein with relation to certain embodiments and applications, those with skill in this art will recognize changes, modifications, alterations and the like which still come within the spirit of the inventive concept, and such are intended to be included within the scope of the invention as expressed in the following claims. It is to be understood that no limitation with respect to the specific methods or processes illustrated herein is intended or should be inferred. In addition, it is to be understood that various presently unforeseen or unanticipated alternatives, modifications, variations or improvements may be subsequently made by those skilled in the art, which are intended to be encompassed by the following claims and those equivalents to which they are entitled.

The invention claimed is:

1. A diaphragm pump protection device for a breastpump, where the breastpump has a pumping device separate from a breast shield, including a shell and a member moveable relative to the shell to expand and contract a volume between the shell and the member moveable relative to the shell, and a motorized drive unit which drives the pumping device, the diaphragm pump protection device comprising: a cover, said cover being received between the shell and the member moveable relative to the shell and mounted upon and traveling with the moveable member, said cover isolating the moveable member relative to the shell from any fluid which may be conveyed from the breast shield to the pumping device.

2. The diaphragm pump protection device of claim 1 wherein said diaphragm pump protection device is flexible.

3. The diaphragm pump protection device of claim 1 wherein said diaphragm pump protection device forms a gasket between said movable member and said shell.

4. The diaphragm pump protection device of claim 1 wherein said moveable member has a circumferential rim upon which said cover is fixed and substantially non-removable therefrom to form a substantially airtight connection.

5. The diaphragm pump protection device of claim 1 wherein said diaphragm pump protection device is made of the same material as the movable member.

6. A pump for generating pressure variations in a breast shield of a breastpump comprising:
a source of pressure in communication with the breast shield;
a programmable controller having an interface for the inputting of programs, said programs instructing said controller to produce different sequences of operation of said source of pressure;
a chamber defined by a shell and a flexible member movable relative to said shell;
a mechanism connected to said movable member which moves said movable member to expand and contract a volume defined within said chamber;
a port in said shell through which fluid moves in response to expansion and contraction of said volume, said fluid movement being communicated to the breast shield; and
a mounted cover between said shell and over said movable member isolating said movable member from fluid which may be communicated from the breast shield.

7. The pump of claim 6 wherein said pump is a diaphragm pump, and said shell has a generally hemispherical interior shape.

8. The pump of claim 7 wherein said cover is flexible.

9. The pump of claim 8 wherein said movable member has a circumferential rim, said cover being fixed to and substantially non-removable from said rim, and said shell has an internal opening defined therein sized to encompass said rim with said cover mounted on said rim in a substantially airtight fit, said cover thereby forming a gasket between said rim and shell.

10. The pump of claim 9 wherein said cover is made of the same material as the movable member.

11. A diaphragm pump for a breastpump having a breast shield, comprising:
a source of pressure in communication with the breast shield;
a programmable controller having an interface for the inputting of programs, said programs instructing said controller to produce different sequences of operation of said source of pressure;
a shell having a generally hemispherical interior shape;
a flexible membrane movable within said hemispherical shape to expand and contract a volume created in a chamber defined between said membrane and shell;
a mechanism connected to said membrane which moves said membrane to expand and contract said volume;
a port in said shell through which air moves in response to expansion and contraction of said volume; and
a flexible cover fixedly mounted between said shell and said membrane which isolates said membrane from fluid which may be conveyed from the breast shield.

12. A diaphragm pump for a breastpump, comprising:
a shell having a generally hemispherical interior shape;
a flexible membrane movable within said hemispherical shape to expand and contract a volume created in a chamber defined between said membrane and shell;
a mechanism connected to said membrane which moves said membrane to expand and contract said volume;
a port in said shell through which air moves in response to expansion and contraction of said volume;
a flexible cover fixedly mounted between said shell and said membrane which isolates said membrane from fluid; and
a one-way valve extending through said movable membrane, said valve allowing exhaustion of air between said movable membrane and said cover mounted thereon.

* * * * *